Aug. 29, 1961 R. S. MOORE Plant Pat. 2,080
MINIATURE ROSE PLANT
Filed Aug. 29, 1960
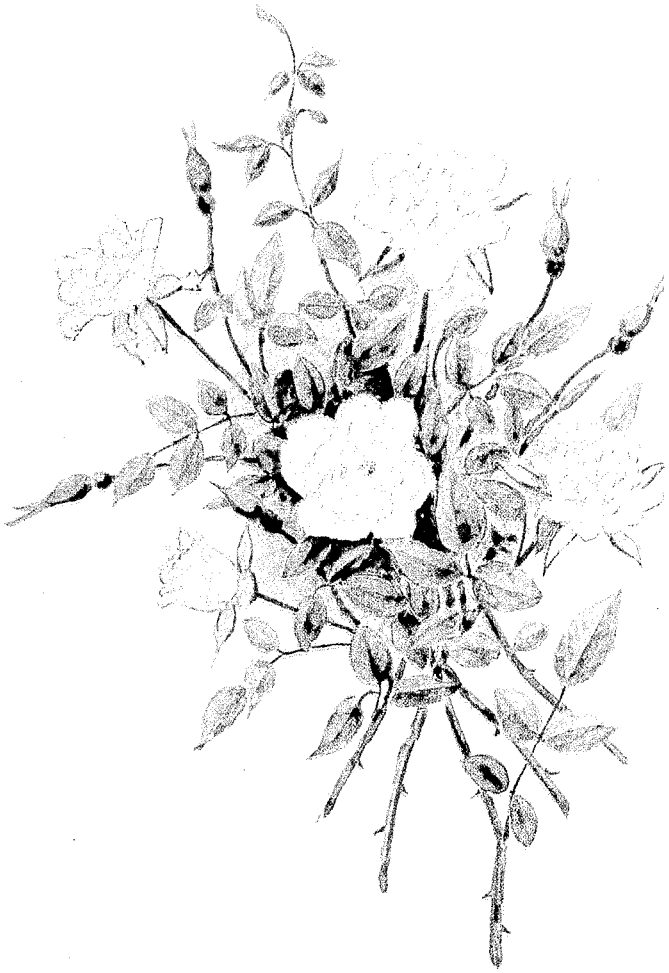
WITNESS
Addison G. Avery
INVENTOR
Ralph S. Moore
Webster & Webster
ATTYS.

United States Patent Office

Plant Pat. 2,080
Patented Aug. 29, 1961

2,080
MINIATURE ROSE PLANT
Ralph S. Moore, Visalia, Calif.
Filed Aug. 29, 1960, Ser. No. 52,751
1 Claim. (Cl. 47—61)

This invention relates to a new and distinct variety of hybrid miniature rose plant of hardy, dwarf, bush type.

Such plant is characterized—as to novelty—by relatively easy propagation from soft wood cuttings; by excellent and vigorous but compact growth which is maintained with a minimum of attention; by abundant foliage; and by bright red, usually fully double, long lasting flowers borne freely all season and in any weather, and which flowers have the unusual habit of fading darker as they age.

As compared with other miniature rose plants the present variety bears flowers which generally resemble the Red Imp (United States Plant Patent No. 1,032) in color, but with a form and size more nearly those of the Dian (United States Plant Patent No. 1,808). Additionally, the flowers of the present variety have a brighter red color, and the foliage is glossier, than the Dwarf King (United States Plant Patent No. 1,577).

The instant variety of miniature rose plant was originated by me, in my nursery located at Visalia, California, and under conditions of careful control and observation, as a cross between an unnamed seedling (*Rosa wichuraiana*×Floradora, both unpatented) as the seed parent, and Little Buckaroo (United States Plant Patent No. 1,726) as the pollen parent. Subsequent to origination of the variety I successfully asexually reproduced it in my nursery, located as aforesaid, by budding as well as cuttings; the reproductions having run true in all respects.

The drawing illustrates a spray including foliage, buds, and flowers.

Referring now specifically to the new and distinct variety of miniature rose plant, the following is a detailed description thereof in outline; all major color plate identifications being—as indicated—either by reference to The British Colour Council Horticultural Colour Chart, or Maerz and Paul Dictionary of Color, except where common terms of color definition are employed.

Type: Hardy; dwarf; bush; seedling; greenhouse; outdoors; cut flowers; garden decoration.
Class: Hybrid miniature.

*Flowers*

Continuity: Continuous.
Fragrance: Slight.
Flowers Borne: Singly to two or three on strong, short stems.
Quantity of bloom: Free, both outdoors and in greenhouse.
Bud:
*Peduncle.*—Medium length; medium heavy; erect; stiff; reddish; numerous red prickles.
*Before calyx breaks.*—Size—small. Form—long; pointed; few and small folaceous appendages on the surface of the bud; stout folaceous parts extending beyond the tip of the bud equal to three-fourths of its length. Color—green.
*As calyx breaks.*—Color—red.
*As first petal opens.*—Size—small. Form—short; pointed. Color—red, both outside and inside. Opening—opens well in any weather.
Bloom:
*Size when fully open.*—Small, averaging 1" to 1½".
*Petalage.*—Double, with from 30 to 40 petals fairly regularly arranged.

*Form.*—High center, globular at first, becoming later and at maturity rolled outward.
Petals: Thick; leather. Inside—satiny to velvety. Outside—satiny.
*Shape.* — Outside — broad lanceolate. Intermediate—lanceolate. Inside—lanceolate.
*Color.*—Newly opened flower from plant grown outdoors (July)—outside and inside surfaces—Chrysanthemum Crimson (824/2), shading to Garnet Lake (828) at petal tips (Horticultural Colour Chart—British Colour Council). These colors may tend to shade lighter depending upon the season. A flower that was open for three days outdoors (July)—outside and inside surfaces—Crimson Lake (824/3), shading darker (824) at petal tips (Horticultural Colour Chart—British Colour Council). The outside surface of the petals may shade to a lighter red, with a slight silvery sheen.
*General color effect.*—Newly opened flower—bright velvety red. Three days open—deeper red. The basal ¼ of the petal frequently white or near white.
*Behavior.*—Persist; fade to a deep crimson purple; opens well in all weather. In wet or overcast weather the petals diminish in brightness.
*Flower longeviety (June).*—Bush in garden—five days or longer. Cut flowers kept at living room temperatures—three to four days, sometimes longer.
Reproductive organs:
*Stamens.*—Few, often none; arranged irregularly; mixed with petaloids.
*Filaments.*—Short; white; few; most with anthers.
*Anthers.*—Small; yellow or near yellow; open at various times.
*Pollen.*—Sparse; yellow.
*Pistils.*—Few to medium number.
*Styles.*—Uneven; short; medium; bunched.
*Stigma.*—White.
*Ovaries.*—All enclosed in calyx.
*Hips.*—None.
*Sepals.*—Permanent; long; spear shaped; green, turning brown. Later peduncle separates from plant and drops off.
*Seeds.*—None.

*Plant*

Foliage:
*Leaves.*—Compound of three to five leaflets; abundant; small; moderately heavy; glossy.
*Leaflets.* — Shape — lanceolate. Apex — acute. Base—round. Margin—serrate. Color: upper surface—normal green (22–L–9, Maerz and Paul Dictionary of Color); under surface—lighter normal green (21–I–6, Maerz and Paul Dictionary of Color). Rachis—medium; upper side grooved; under side moderately prickly, one to three tiny thorns. Stipules—medium length; medium width; with short points turning out at an angle of about 45 degrees.
Growth:
*Habit.*—Dwarf; bushy; much branched; breadth substantially equals height.
*Growth.*—Free; vigorous.
*Canes.*—Medium.
*Main stems.* — Color — green. Thorns — reddish brown (7–L–12, Maerz and Paul Dictionary of Color); several; medium length; straight, with oval base, sometimes slightly hooked downward. Prickles—none. Hairs—none.

*Branches.*—Color—green. Thorns—several; hooked downward, with oval base. Prickles—none. Hairs—none.

*New shoots.*—Color—bright green, sometimes tinted red. Thorns—slightly hooked downward, with long narrow base. Prickles—none. Hairs—none.

The miniature rose plant and its flowers as herein described may vary in slight detail due to climatic and soil conditions under which the variety may be grown; the present description being of the variety as grown at Visalia, California.

The following is claimed:

A new and distinct variety of rose plant of the hybrid miniature class and hardy, dwarf, bush type, characterized by relatively easy propagation from soft wood cuttings, by excellent and vigorous but compact growth which is maintained with a minimum of attention, by abundant foliage, and by bright red, usually fully double, long lasting flowers borne freely all season and in any weather, and which flowers have the unusual habit of fading darker as they age; further characterized by flowers which generally resemble the Red Imp in color but with a form and size more nearly those of the Dian; and additionally characterized by glossier foliage and by flowers having a brighter red color than the Dwarf King.

No references cited.